United States Patent
Stieg et al.

[19]

[11] Patent Number: 6,117,684

[45] Date of Patent: Sep. 12, 2000

[54] BACKPRESSURE REGULATING FLOW CELL THAT MAY BE UTILIZED WITH SENSOR

[75] Inventors: Scott W. Stieg, Milwaukee; James A. Dittmar, Waukesha; Karin L. Bogren, Milwaukee, all of Wis.

[73] Assignee: Zellweger Analytics, Inc., France

[21] Appl. No.: 09/247,193

[22] Filed: Feb. 9, 1999

[51] Int. Cl.[7] .............................. G01N 35/08; C12Q 1/00; C12M 1/40

[52] U.S. Cl. ............................ 436/52; 435/4; 435/287.1; 435/287.9; 435/817; 204/409; 422/81

[58] Field of Search ..................... 435/4, 287.1, 287.9, 435/288.7, 817; 422/81, 82, 82.01, 82.02, 82.03; 436/52, 53; 204/403.409; 73/64, 56, 864.81, 864.91; 356/246, 440; 250/576

[56] References Cited

U.S. PATENT DOCUMENTS 2,983,184  5/1961  Ferrari .
3,020,795  2/1962  McKinney et al. .
3,690,833  9/1972  Ferrari .
3,711,206  1/1973  Moran .
3,770,608  11/1973  Kelch et al. .
5,045,284  9/1991  Smith et al. .
5,711,862  1/1998  Sokoda et al. .

OTHER PUBLICATIONS

Jenway Ltd., Operations Manual "Flame Photometer PFP 7", pp. 3–5; 11; 18; 20–21; 37 (No date provided).

*Primary Examiner*—William H. Beisner
*Attorney, Agent, or Firm*—Fletcher, Yoder & Van Someren

[57] ABSTRACT

A flow cell for use in an analytical system of the type that may be used to test water samples for specific analytes. The flow cell reduces or eliminates the effects of backpressure on a liquid stream passing through the flow cell. This allows a sensor to be incorporated with the flow cell and enables the sensor to provide consistent output with respect to the analyte being tested without introducing signal error due to backpressure fluctuations.

18 Claims, 2 Drawing Sheets

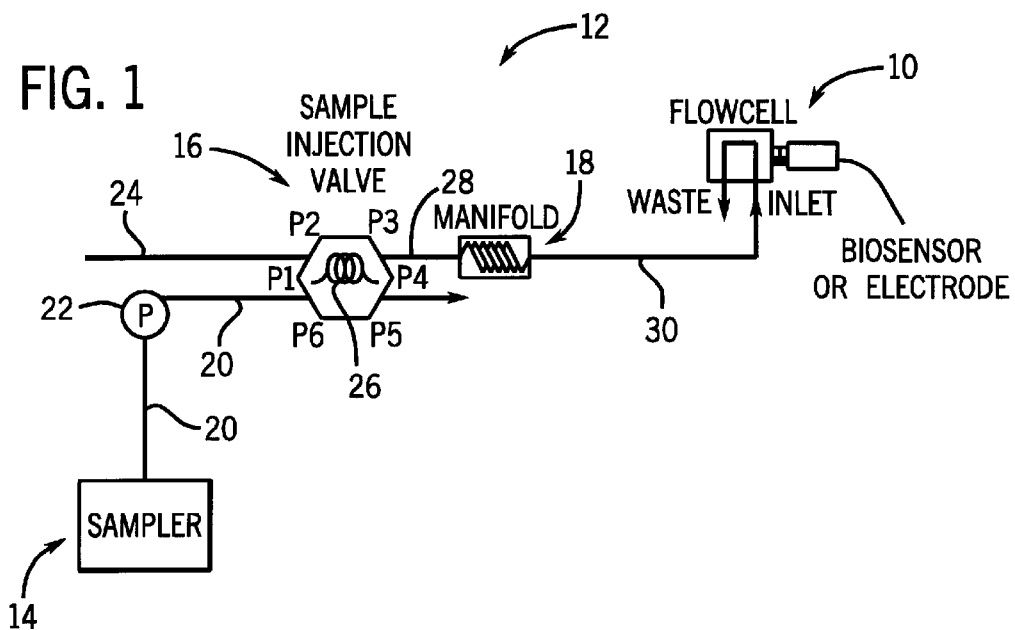
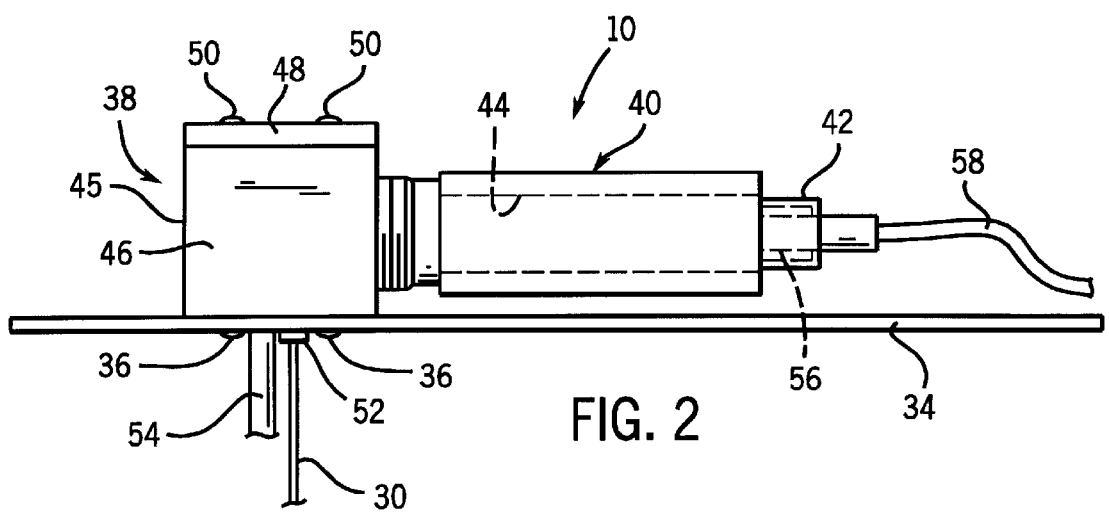

BACKPRESSURE REGULATING FLOW CELL THAT MAY BE UTILIZED WITH SENSOR

FIELD OF THE INVENTION

The present invention relates generally to analytical systems for determining the presence of specific constituents in a liquid stream, and particularly to a flow cell that may be combined with a sensor to measure, for example, analytes dissolved in water.

BACKGROUND OF THE INVENTION

A variety of analytical systems are used in the detection of specific constituents within a liquid sample. For example, a flow injection analysis system may be used to measure a specific analyte dissolved in water. In any analytical system, however, a sensor typically is used to measure or detect the specific constituent of interest.

A typical sensor may be in the form of a probe that acts as a transducer able to convert the presence or concentration of an analyte in the liquid sample to data of use to an analyst. Commonly, sensors that do not dissolve in the sample are referred to as electrodes. A variety of electrode sensors are used in the field of water analysis. In general, these electrodes are named after the analyte to which they respond. For example, electrode sensors that respond to ions in solution are called ion-selective electrodes. Further, they may respond only to a specific analyte, such as fluoride or glucose. Also, if the sensor's mechanism of sensing depends on an enzyme immobilized onto the surface of the electrode, the sensor is referred to as an enzyme electrode or a biosensor. Such biosensors often sense as their analytes, the "substrate" or analyte compound whose reaction with various reactants is catalyzed by the enzyme.

The above-described sensors typically are designed with an analyte-sensitive surface on one exposed end of the sensor. This surface may then be placed in contact with a potential, desired constituent, such as an analyte, in the liquid sample in various ways. For example, the sensor may be dipped into a sample solution or the sensor may be exposed to a flowing stream. In either case, the electrode is calibrated to output a response, e.g. a current or a voltage, proportional to change in concentration of the constituent of interest in the sample solution.

Preferably, the change in response or output of the electrode is due only to changes in the analyte concentration within the sample. When a change in the output signal is caused by something other than a corresponding change in concentration of the specific constituent of interest, the change results in an error signal.

Generally, the error signal may rise from a change in the sensitivity of the electrode or from an interference. For example, changes in the total ionic strength and/or temperature of the analyte solution may affect the sensitivity of the sensor. However, pressure changes, interfering compounds, gas bubbles, static electrical discharges, and changes in the resistivity of the electrode can provide an interference that leads to an error signal. One of the most difficult error signals to control is that which results from pressure changes acting on the liquid sample. Water solutions, for example, are incompressible and instantly transmit forces and pressures to all surfaces exposed to the solution, including the exposed sensor surface.

When sensing the presence of a specific constituent within a static liquid sample, the sensor is held steady while submerged in the liquid sample until a sufficient decrease occurs in the pressure related error signal. However, such batch measurements are inefficient due to the time required in waiting for a sufficient decrease in the pressure induced error signal. Generally, it is more efficient to test a liquid sample by flowing the liquid sample in a stream past the sensitive surface of the sensor. This may be accomplished by mounting the sensor in a flow cell.

A conventional flow cell consists of a sample stream inlet that opens into a chamber in which one wall is defined by the sensitive surface of the sensor. The liquid stream continually flows past the sensor to a waste outlet and on to waste. With this system, multiple samples can be pumped in series through the flow cell and past the sensor without movement of the sensor from one sample solution to another.

Because any perturbations to the flowing liquid stream can create pressure changes that cause the sensor to create error signals, the design of the flow path is important for accurate analysis of the liquid stream. Conventional flow cells do little to facilitate consistent, accurate sensor output by eliminating the potential for pressure changes in the liquid stream. It would be advantageous, for example, to eliminate sources of change in backpressure that result from perturbation of the liquid stream downstream from the sensor.

SUMMARY OF THE INVENTION

The present invention features a system for detecting the presence of a substance in a flowing liquid stream. The system comprises a flow cell having a housing. The housing includes a flow-through path, a drain chamber, and an overflow separating the flow-through path from the drain chamber. A sensor is disposed in communication with the flow-through path. Also, the overflow remains at a constant height above the sensor so that the liquid between the sensor and the overflow is the only liquid affecting the backpressure acting on the sensor.

According to another aspect of the invention, a flow cell is provided for regulating a backpressure at a specific sensor location. The flow cell comprises a housing including a flow-through path, a drain chamber, an outlet chamber and an overflow region. The flow-through path includes an inlet, an outlet and a sensor region disposed between the inlet and the outlet at a position below the outlet. The drain chamber includes a chamber inlet and a chamber outlet, wherein the chamber inlet is disposed proximate the flow-through path outlet. The outlet chamber is disposed at a higher elevation than the flow-through path and the drain chamber, but it is in fluid communication with both to facilitate venting of gas from the liquid stream. The venting helps prevent pressure changes as the liquid stream flows from the flow-through path over the overflow region into the drain chamber.

According to another aspect of the invention, a method is provided for sensing a specific constituent in a liquid stream. The method includes directing a liquid sample stream upwardly along a flow path to an overflow region. The method further includes draining the liquid sample stream as it passes over the overflow region. Additionally, the method includes sensing the liquid sample stream for a specific constituent, as it flows along the flow path. The sensing occurs at a location that remains a constant distance beneath the overflow region.

BRIEF DESCRIPTION OF THE DRAWINGS

The invention will hereafter be described with reference to the accompanying drawings, wherein like reference numerals denote like elements, and:

FIG. 1 is a schematic illustration of a flow injection analysis system utilizing a backpressure regulating flow cell and sensor, according to a preferred embodiment of the present invention;

FIG. 2 is a front view of a flow cell combined with a sensor, according to a preferred embodiment of the present invention;

FIG. 3 is a front view similar to FIG. 2, but showing internal features of the flow cell;

DETAILED DESCRIPTION OF THE PREFERRED EMBODIMENTS

Figure 4:
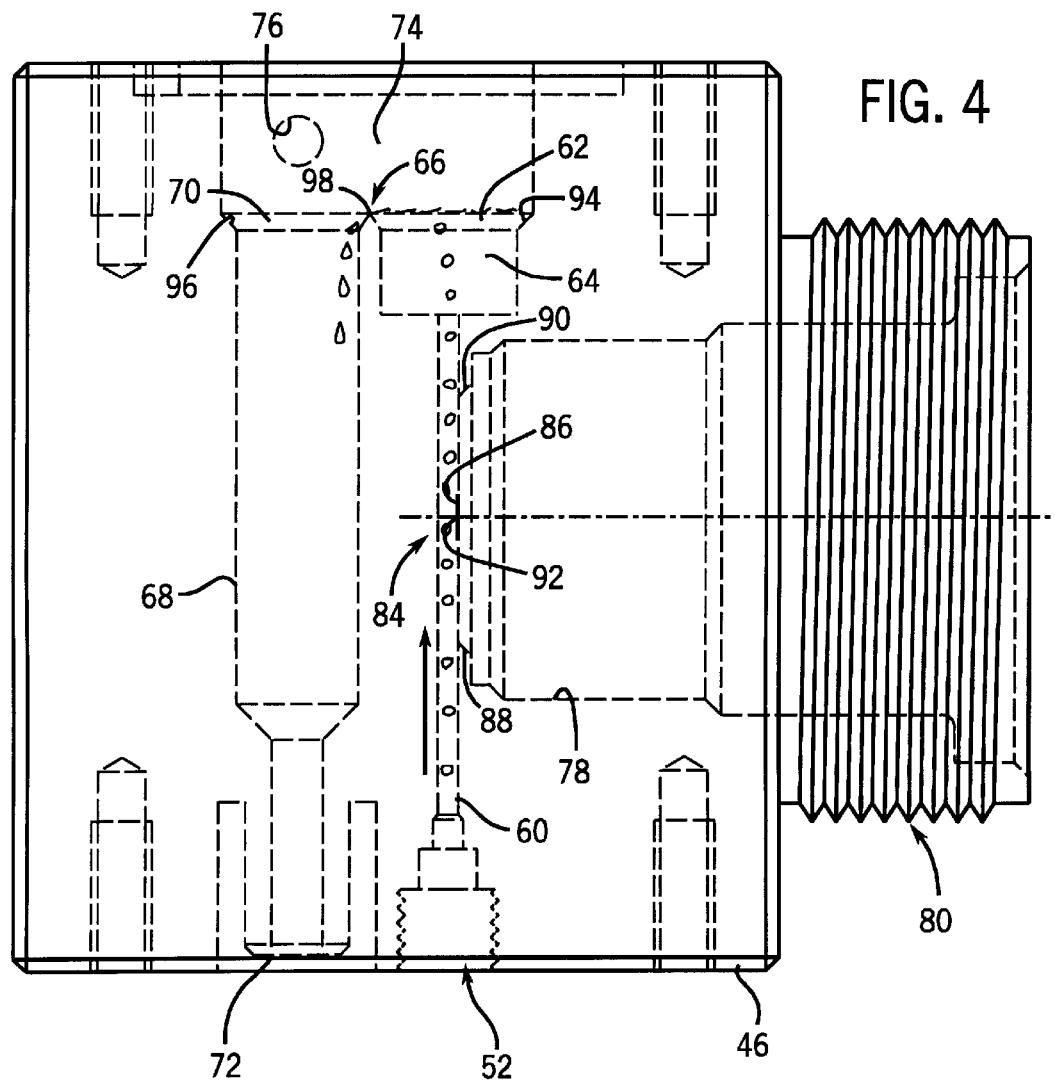
FIG. 4 is a front view of the body of the flow cell illustrated in FIG. 3.

Referring generally to FIG. 1, a flow cell system 10 is illustrated as integrated into an overall analytical system 12. In this exemplary embodiment, analytical system 12 comprises a flow injection analysis system. Analytical system 12 may include a variety of components, such as a sampler 14, a multiport injection valve 16, a manifold 18 and flow cell system 10.

In operation, a sample to be analyzed is pumped from sampler 14 to a port labeled P6 of multiport injection valve 16 through a flow line 20. Typically, the sample is pumped through flow line 20 by an appropriate pump 22. At this initial stage, any sample flowing through multiport injection valve 16 exits sample injection valve 16 at exit port P5 and is allowed to flow to waste or a subsequent valve. The multiport injection valve is said to be at an "inject" state during this initial stage.

Simultaneously, a buffer or carrier liquid flows into multiport injection valve 16 via a carrier line 24 that directs the carrier or buffer liquid into port P2. From port P2, the carrier liquid flows through a sample loop 26 that is connected between ports P1 and P4. From sample loop 26, the carrier liquid exits multiport injection valve 16 through a port P3, and continues flowing through a flow line 28, through manifold 18, through a flow line 30 and through flow cell system 10 to waste.

Typically, as the sample begins to flow through valve 16 during the inject state, the valve state of multiport injection valve 16 is changed so that the sample flows into sample loop 26. During this "load" state, the sample fills sample loop 26 and any excess flow exits valve 16 through port P5. During loading of the sample loop, the buffer/carrier liquid bypasses the sample loop 26 and flows directly through valve 16 until it exits at port P3.

Upon filling of sample loop 26 with a given sample, the valve state of multiport injection valve 16 is changed back to the inject state. In this latter state, the buffer/carrier liquid again is directed through the sample loop 26, causing the sample within sample loop 26 to flow through manifold 18 and on through flow cell system 10. Manifold 18 facilitates the creation of a precisely shaped sample zone that passes through flow cell system 10. As the sample flows through flow cell system 10, a constituent of the sample, e.g. an analyte of interest, is detected.

The above-described flow injection analysis system is one example of analytical system 12 that can be utilized with flow cell system 10, according to the present invention. The specific components, such as sampler 14, pump 22, sample injection valve 16 and manifold 18 are known to those of ordinary skill in the art, and the specific components and arrangement of components can be established according to the types of samples being tested as well as the parameters set forth by the manufacturers of the system components.

Referring generally to FIG. 2, a front view of a preferred embodiment of flow cell system 10 for use in a variety of analytical systems 12, is illustrated. Flow cell system 10 is mounted to a support structure 34 by, for instance, a plurality of fasteners 36, such as screws.

Flow cell system 10 comprises a flow cell 38, a flow cell nut 40 and a sensor 42. Flow cell nut 40 is mounted to flow cell 38 by, for instance, threaded engagement. Additionally, flow cell nut 40 includes a hollow interior 44 for receiving sensor 42.

Flow cell 38 includes a flow cell housing 45 having a flow cell body 46 and a flow cell cover 48 that is attached to flow cell body 46 by, for instance, a plurality of fasteners 50, such as screws. Preferably, flow cell housing 45 is made from an inert, polymeric material. Flow cell housing 45 also includes a liquid stream inlet 52 through which liquid, including the liquid sample to be tested, passes from flow line 30 into flow cell 38. A waste line 54 also is connected to flow cell 38 to conduct the liquid stream away from flow cell 38 after passage therethrough.

Sensor 42 may comprise a variety of sensors depending on the sample constituent to be detected. For example, sensor 42 may comprise a probe 56 that outputs a signal through a lead line 58 to an appropriate data station (not shown). Furthermore, sensor 42 may comprise an electrode, or specifically a biosensor, depending on the constituent being sensed. A biosensor, such as an enzyme-based biosensor, can be used to detect an analyte species within a liquid stream. The sensor typically is designed and calibrated to sense a specific analyte, e.g., fluoride, in which case it can be referred to as a fluoride-specific sensor.

Figure 5:
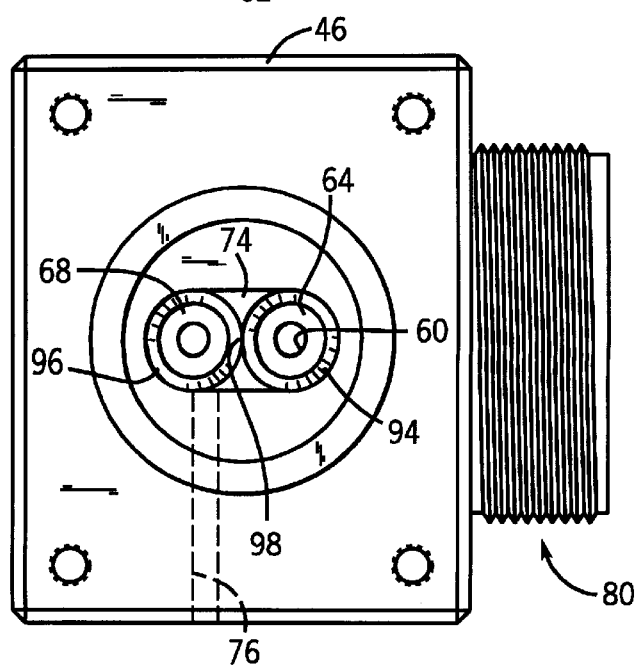
FIG. 5 is a top view of the flow cell body illustrated in FIG. 4.

Referring generally to FIGS. 3–5, the internal features of flow cell 38 are illustrated. Flow cell housing 45 includes a flow-through path 60 that extends upwardly from liquid stream inlet 52 to a liquid stream outlet 62. Preferably, flow-through path 60 is oriented generally vertically when flow cell system 10 is mounted to support structure 34. Also, flow-through path 60 preferably includes an expanded region 64 proximate liquid stream outlet 62.

As the liquid stream moves upwardly through flow path 60, it ultimately flows over an overflow or overflow region 66. Once the liquid stream passes over overflow 66, it enters a drain chamber 68 via a drain chamber inlet 70. When the liquid stream enters drain chamber 68, it freely falls downwardly until exiting flow cell 38 via a drain chamber outlet 72. From outlet 72, the liquid is conducted to waste by waste line 54.

Drain chamber 68 is sized to have sufficient capacity for handling the volume of liquid in the liquid stream without hindering any of the liquid as it flows across overflow 66. This ensures that no changes in backpressure result due to potential perturbations on the liquid stream flowing to waste once it crosses overflow 66. Preferably, drain chamber 68 is oriented generally vertically such that it is substantially parallel with flow-through path 60.

An outlet chamber 74 is disposed in fluid communication with flow-through path 60 and drain chamber 68 at a elevation higher than flow-through path 60 and drain chamber 68. Preferably, outlet chamber 74 is disposed directly above liquid stream outlet 62 and drain chamber inlet 70. Outlet chamber 74 provides an air space above the overflow 66 to eliminate the potential for interference with the liquid stream, that could lead to backpressure changes, as it flows across overflow 66. Additionally, outlet chamber 74 preferably includes a vent 76 to vent gas that may be released from the liquid stream as it passes upwardly through flow path 60. This prevents accumulation of gas in outlet chamber 74 that also could lead to changes in backpressure.

Flow cell 38 further includes a lateral opening 78 for receiving flow cell nut 40 and sensor 42. Lateral opening 78 may be coupled to, for example, a threaded region 80 at which flow cell nut 40 is threadably engaged with flow cell 38. Lateral opening 78 allows flow cell nut 40 and sensor 42 to be brought into proximity with flow-through path 60. Typically, a seal 82 is disposed between flow cell nut 40 and flow-through path 60 so that sensor 42 may be sealed in fluid communication with flow-through path 60 at a sensor region 84. Sensor region 84 is located between liquid stream inlet 52 and liquid stream outlet 62. This location and a sensory surface 86 of sensor 42 are maintained at a constant distance beneath overflow 66.

An exemplary sensory surface 86 is an analyte-sensitive surface on one exposed end of sensor 42. As illustrated best in FIG. 4, flow cell nut 40 includes an engagement end 88 which engages an opening 90 that provides access to flow-through path 60. Sensory surface 86 is located at engagement end 88 and is disposed in contact with the liquid stream flowing through flow-through path 60 when flow cell nut 40 and sensor 42 are properly engaged with flow cell 38. Specifically, sensory surface 86 and particularly a geometric center 92 of sensory surface 86 is held in sensor region 84 at a fixed distance beneath overflow 66.

As best illustrated in FIG. 5, liquid stream outlet 62 preferably includes an outwardly chamfered edge 94. Similarly, drain chamber inlet 70 also preferably includes a chamfered edge 96. In the embodiment illustrated, chamfered edge 96 abuts chamfered edge 94 to form a peak 98 therebetween. Chamfered edges 94 and 96, as well as peak 98, facilitate the transfer of the liquid stream from flow-through path 60 to drain chamber 68. Peak 98 helps reduce the effects of surface tension acting on the liquid sample stream to prevent minor fluctuations in backpressure. Additionally, an appropriate surfactant can be added to the liquid stream to further reduce the effects of surface tension.

During operation of an analytical system, such as the system illustrated in FIG. 1, a carrier fluid flows through analytical system 12 and through flow cell system 10 until the sample to be tested is injected into the carrier stream. Initially, the liquid carrier stream flows through the system and enters flow cell 38 via liquid stream inlet 52. The liquid stream continues upwardly through flow-through path 60 and past sensory surface 86 of sensor 42. The liquid stream contacts sensory surface 86 as it flows therethrough and continues upwardly until it begins to fill expanded region 64 of flow-through path 60. When expanded region 64 is filled, a given backpressure is established that remains constant throughout the test procedures.

The unique design of the flow cell ensures a very consistent backpressure, because any additional fluid moving upwardly through flow-through path 60 causes excess liquid in flow-through path 60 to move across overflow 66. Once the excess liquid passes peak 98 it effectively is dropped into drain chamber 68. Thus, any outside influences on the liquid stream after passing peak 98 are not translated to flow-through path 60 and sensory surface 86. After crossing overflow 66, the liquid stream simply moves through drain chamber 68 and exits flow cell 38 via waste line 54. Thus, the initial carrier liquid establishes a consistent backpressure acting on sensory surface 86 that remains unchanged as the sample liquid stream passes along sensory surface 86. This facilitates consistent accurate measurements with respect to each sample of multiple samples that may be passed through flow cell 38.

It will be understood that the foregoing description is of preferred embodiments of this invention, and that the invention is not limited to the specific forms shown. For example, a variety of analytical systems may be utilized with the flow cell system; the sensor may be of various configurations depending on mounting requirements and the specific constituent or constituents being tested; the flow-through path and drain chamber potentially may be established in a non-vertical orientation; the specific structure of the flow cell and its internal configuration may be adjusted; and the flow cell may be made from a variety of materials. These and other modifications may be made in the design and arrangement of the elements without departing from the scope of the invention as expressed in the appended claims.

What is claimed is:

1. A system for detecting the presence of a substance in a flowing liquid stream, comprising:

a flow cell including a housing having a flow-through path, a drain chamber, and an overflow separating the flow-through path from the drain chamber; and a sensor disposed in communication with the flow-through path, wherein the overflow remains at a constant height above the sensor wherein the flow-through path is oriented generally vertically and includes an expanded region disposed above the sensor.

2. The system as recited in claim 1, wherein the overflow includes a chamfered edge extending from the flow-through path to an overflow peak to facilitate transition of the flowing liquid stream from the flow-through path to the drain chamber.

3. The system as recited in claim 1, wherein the housing further comprises an outlet chamber disposed above the flow-through path and the drain chamber.

4. The system as recited in claim 3, wherein the outlet chamber includes a vent disposed above the overflow to allow gases to exit the flow cell.

5. The system as recited in claim 1, wherein the sensor comprises a biosensor.

6. The system as recited in claim 1, wherein the sensor comprises an immobilized enzyme sensor able to detect a specific analyte in the flowing liquid stream.

7. A flow cell for regulating a backpressure at a specific sensor location, comprising:

a housing including:

a flow-through path having an inlet, an outlet and a sensor region disposed therebetween;

a drain chamber having a chamber inlet and a chamber outlet;

an outlet chamber disposed in fluid communication with and at a higher elevation than the flow-through path and the drain chamber;

an overflow region disposed between the flow-through path and the drain chamber, wherein during operation a fluid flows over the overflow region as it transitions from the flow-through path to the drain chamber; and a lateral opening disposed generally transversely to the flow-through path, the lateral opening being designed to receive a sensor.

8. The flow cell as recited in claim 7, wherein the housing further includes a vent in fluid communication with the outlet chamber to vent excess gas.

9. The flow cell as recited in claim 7, wherein the outlet of the flow-through path includes a chamfered edge.

10. The flow cell as recited in claim 9, wherein the chamber inlet of the drain chamber includes a second chamfered edge.

11. The flow cell as recited in claim 10, wherein the chamfered edge and the second chamfered edge are contiguous.

12. The flow cell as recited in claim 7, wherein the housing comprises an inert, polymeric material.

13. A method for sensing a specific constituent in a liquid stream, comprising:

directing a liquid sample stream upwardly along a flow path to an overflow region;

draining the liquid sample stream as it passes over the overflow region; and sensing the liquid sample stream for a specific constituent, along the flow path, at a location that remains a constant distance beneath the overflow region;

establishing a desired backpressure by directing the liquid sample stream into an expanded region intermediate the location at which the liquid sample stream is sensed and the overflow region.

14. The method as recited in claim 13, wherein directing comprises directing an analyte stream.

15. The method as recited in claim 14, wherein sensing includes sensing the analyte stream with a biosensor.

16. The method as recited in claim 15, further comprising heating the analyte stream to above room temperature prior to sensing the analyte stream.

17. The method as recited in claim 15, further comprising mixing the analyte stream with a surfactant.

18. The method as recited in claim 15, further comprising venting gas expelled from the analyte stream.

* * * * *